US008722374B2

(12) United States Patent
Leukes et al.

(10) Patent No.: US 8,722,374 B2
(45) Date of Patent: May 13, 2014

(54) PRODUCTION OF SECONDARY METABOLITES USING CAPILLARY MEMBRANES

(75) Inventors: Winston Daniel Leukes, Sea Point (ZA); P. G. Lourens, legal representative, Cape Town (ZA); Sheena Janet Fraser, Sea Point (ZA); Wade Edwards, Fish Hoek (ZA)

(73) Assignee: Synexa Life Science (Proprietary) Limited, Cape Town (ZA)

( * ) Notice: Subject to any disclaimer, the term of this patent is extended or adjusted under 35 U.S.C. 154(b) by 752 days.

(21) Appl. No.: 11/988,071

(22) PCT Filed: Jun. 30, 2006

(86) PCT No.: PCT/IB2006/052201
§ 371 (c)(1),
(2), (4) Date: Jan. 11, 2010

(87) PCT Pub. No.: WO2007/004170
PCT Pub. Date: Jan. 11, 2007

(65) Prior Publication Data
US 2010/0159555 A1    Jun. 24, 2010

(30) Foreign Application Priority Data
Jun. 30, 2005  (ZA) ................................. 2005/05315

(51) Int. Cl.
*C12P 1/04*  (2006.01)
*C12P 1/00*  (2006.01)

(52) U.S. Cl.
USPC ........................................... 435/170; 435/41

(58) Field of Classification Search
None
See application file for complete search history.

(56) References Cited

U.S. PATENT DOCUMENTS

| 4,804,628 | A |   | 2/1989 | Cracauer et al. |
| 4,910,139 | A | * | 3/1990 | Chang et al. ................... 435/144 |
| 4,988,443 | A | * | 1/1991 | Michaels et al. .............. 210/611 |
| 5,480,552 | A | * | 1/1996 | Soltys et al. .................. 210/645 |
| 5,500,352 | A | * | 3/1996 | Lopez ............................. 435/44 |

(Continued)

FOREIGN PATENT DOCUMENTS

| EP |  0112812 A2 * | 7/1984 | ............... C12M 1/12 |
| EP |  0 761 608 A2 | 3/1997 | |
| WO |  WO-02/094979 A2 | 11/2002 | |

OTHER PUBLICATIONS

The Normal Bacterial Flora of Humans (last viewed on Oct. 19, 2011).*

(Continued)

*Primary Examiner* — Alexander Kim
(74) *Attorney, Agent, or Firm* — Nelson Mullins Riley & Scarborough LLP; Anthony A. Laurentano

(57) ABSTRACT

The invention provides methods of producing secondary metabolites and under recombinant products oxygen-limited or anaerobic culture conditions. The methods include providing a porous substrate having a first side and a second side and which has a biofilm of microorganisms attached to the first side thereof, and causing a nutrient solution to flow through the biofilm and the substrate in a direction from the first side thereof to the second side thereof under oxygen-limited or anaerobic culture conditions. The microorganisms include *Clostridium* sp., *Bacillus* sp., *Pseudomonas* sp. *Vibrio* sp., *Serratia* sp., *Rhodopseudomonas* sp., *Anaeromyxobacter* sp., *Desulphovibrio* sp., and *Candida* sp., *Lactococcus lactis, Escherichia coli, Bacillus subtillus, Pichia* sp., *Candida* sp., *Hansenula polymorpha* and *Saccharomyces cerevisiae*.

20 Claims, 7 Drawing Sheets

(56) References Cited

U.S. PATENT DOCUMENTS

| | | | | |
|---|---|---|---|---|
| 5,593,886 | A | * | 1/1997 | Gaddy ........................ 435/252.7 |
| 5,833,896 | A | * | 11/1998 | Jacobs et al. .................... 264/41 |
| 5,945,002 | A | * | 8/1999 | Leukes et al. ................. 210/651 |
| 6,235,196 | B1 | * | 5/2001 | Zhou et al. .................... 210/605 |

OTHER PUBLICATIONS

Aspartame, Methanol and Formaldehyde Relationship (last viewed on Oct. 19, 2011).*
Nagata et al., Cross-flow Membrane Microfiltration of a Bacterial Fermentation Broth, Biotechnology and Bioengineering, 1989, vol. 34, pp. 447-466.*
Porter, Mark C., Handbook of Industrial Membrane Technology., Noyes Publications, 1990, p. 401.*
Tharakan et al., Operation and Pressure Distribution of Immobilized Cell Hollow Fiber Bioreactors., Biotechnology and Bioengineering (1986), vol. 28, pp. 1064-1071.*
Slime mold (last viewed on Jul. 2, 2012).*
Aspergillus (last viewed on Jul. 2, 2012).*
Fungal Lifecycle (last viewed on Jul. 2, 2012).*
Devereux et al., Membrane Separation of Protein Precipitates: Studies with Cross Flow in Hollow Fibers., Biotechnology and Bioengineering (1986), vol. 28, pp. 422-431.*
Kwon et al. Increase of Xylitol Productivity by Cell-Recycle Fermentation of *Candida tropicalis* Using Submerged Membrane Bioreactor., Journal of Bioscience and Bioengineering (2006) vol. 101, pp. 13-18.*
Fenge et al., Cell Culture Technology for Pharmaceutical and Cell-Based Therapies, Edited by Sadettin S . Ozturk and Wei-Shou Hu, CRC Press (2006), pp. 155-224.*
Solomon MS, Membrane bioreactor production of lignin and manganese peroxidase., (2001), Cape Technikon Theses and Dissertation, paper 148, pp. 1-144.*
Puzanov, Taya, Continuous Production of Lactic Acid in a Membrane Bioreactor (1999), A thesis submitted for Mater of Applied Science at University of Toronto, pp. 1-126.*
Strathmann H., Membrane Separation Processes: Current Relevance and Future Opportunities., AIChE Journal, (2001), vol. 47, pp. 1077-1087.*
Chang et al., Experimental assessment of filtration of biomass with transverse and axial fibres; Chemical Engineering Journal., (May 28, 2002), vol. 87, pp. 121-127.*
Mourato (Microfiltration and Nanofiltration, posted on website on Jan. 13, 2010).*
Omaha (2001) Handbook of Public Water Systems, Second Edition, HDR Engineering Inc., John Wiley & Sons, Inc. p. 489.*
Bernheimer, A.W. et al., "Nature and Properties of a Cytolytic Agent Produced by *Bacillus subtilis*," *Journal of General Microbiology*, vol. 61:361-369 (1970).
Cooper, D.G. et al., "Enhanced Production of Surfactin from *Bacillus subtilis* by Continuous Product Removal and Metal Cation Additions," *Applied and Environmental Microbiology*, vol. 42(3):408-412 (1981).
Davis, D.A. et al., "The application of foaming for the recovery of Surfactin from *B. subtilis* ATCC 21332 cultures," *Enzyme and Microbial Technology*, vol. 28:346-354 (2001).
Davis, D.A. et al., "The produciton of Surfactin in batch culture by *Bacillus subtilis* ATCC 21332 is strongly influenced by the conditions of nitrogen metabolism," *Enzyme and Microbial Technology*, vol. 25:322-329 (1999).
de Vos, Willem M., "Gene expression systems for lactic acid bacteria," *Current Opinion in Microbiology*, vol. 2:289-295 (1999).
Georgiou, George et al., "Surface-active Compounds from Microorganisms," *Bio/Technology*, vol. 10:60-65 (1992).
Heinemann, Bernard et al., "Influence of Dissolved Oxygen Levels on Production of L-Asparaginase and Prodigiosin by *Serratia marcescens*," *Applied Microbiology*, vol. 19(5):800-804 (1970).
Kuipers, Oscar P. et al., "Controlled overproduction of proteins by lactic acid bacteria," *Trends Biotechnol.*, vol. 15(4):135-140 (1997).
Madsen, Søren M. et al., "Molecular characterization of the pH-inducible and growth phase-dependent promoter P170 of *Lactococcus lactis*," *Molecular Microbiology*, vol. 32(1):75-87 (1999).
Nakano, Michiko M. et al., "Adaptation of *Bacillus subtilis* to oxygen limitation," *FEMS Microbiology*, vol. 157:1-7 (1997).
Studier, F. William, "Protein production by auto-induction in high-density shaking cultures," Protein Expression and Purification, vol. 41:207-234 (2005).
Vollenbroich, Dirk et al., "Mechanism of Inactivation of Enveloped Viruses by the Biosurfactant Surfactin from *Bacillus subtilis*," Biologicals, vol. 25:289-297 (1997).
Vollenbroich, Dirk et al., "Antimycoplasma Properties and Application in Cell Culture of Surfactin, a Lipopeptide Antibiotic from *Bacillus subtilis*," Applied and Environmental Microbiology, vol. 63(1):44-49 (1997).
Wei, Yu-Hong et al., "Enhancement of surfactin production in iron-enriched media by *Bacillus subtilis* ATCC 21332," Enzyme and Microbial Technology, vol. 22:724-728 (1998).
Wei, Yu-Hong et al., "Identification of Induced Acidification in Iron-Enriched Cultures of *Bacillus subtilis* during Biosurfactant Fermentation," Journal of Bioscience and Bioengineering, vol. 96(2):174-178 (2003).
Wei, Yu-Hong et al., "Optimizing Iron Supplement Strategies for Enhanced Surfactin Produciton with *Bacillus subtilis*," Biotechnol. Prog., vol. 20:979-983 (2004).
Yeh, Mao-Sung et al., "Bioreactor design for enhanced carrier-assisted surfactin production with *Bacillus subtilis*," Process Biochemistry, vol. 41:1799-1805 (2006).
Zhou, Xu Xia et al., "The nisin-controlled gene expression system: Construction application and improvements," Biotechnology Advances, vol. 24:285-295 (2006).

* cited by examiner

PRODUCTION OF SECONDARY METABOLITES USING CAPILLARY MEMBRANES

RELATED APPLICATIONS

This application is a 35 U.S.C. 371 national stage filing of International Application No. PCT/IB2006/052201, filed 30 Jun. 2006, which claims priority to South Africa Patent Application No. 2005/05315 filed on 30 Jun. 2005 in South Africa. The contents of the aforementioned applications are hereby incorporated by reference.

FIELD OF INVENTION

THIS INVENTION relates to the production of secondary metabolites or recombinant products. In particular, it relates to methods for producing secondary metabolites and/or recombinant products under oxygen-limited conditions or anaerobic conditions, and to apparatus for producing said secondary metabolites and/or recombinant products under oxygen-limited conditions or anaerobic conditions.

BACKGROUND TO INVENTION

Secondary Metabolites

Most technologies used for the production of natural products have been developed to improve oxygen mass transfer in aerobic fermentations. Few anaerobes have been exploited for their ability to produce secondary metabolites. Anaerobic fermentations have primarily been developed for waste water treatment and bioprocesses such as organic acid or ethanol production.

Secondary metabolites are produced on differentiation in solid culture and/or the stationary phase in liquid culture. They are typically produced in submerged liquid culture in batch or fed-batch mode. The events that are typically followed in batch culture are:
1. An inoculum is introduced into the prepared bioreactor. It typically demonstrates a lag phase while the organism or culture adapts to its environment.
2. Once the organisms begin to grow, typically by binary fission, an exponential phase ensues, with the culture biomass concentration increasing rapidly while nutrients are consumed. Primary metabolites and metabolic waste products accumulate.
3. Eventually, the nutrients in the culture are depleted and waste products accumulate to an extent where the culture no longer increases in biomass concentration. This phase of no growth is called the stationary phase. It is during this time that secondary metabolites are produced. Fed-batch culture involves the addition of nutrients at a low level and or dilution of waste products to extend the stationary phase.

Factors that affect the volumetric productivity of bioreactors for secondary metabolite production include: low shear environment, high biomass concentration, differentiation of the culture, the presence of a solid substrate for immobilization of the biomass, extended production phase and good nutrient mass transfer. While systems have been developed for the enhanced production of secondary metabolites under aerobic culture conditions, the efficient production of secondary metabolites under anaerobic conditions has been mostly ignored.

The secondary metabolites of anaerobic microorganisms are of high relevance to the life sciences. Since anaerobic microorganisms typically inhabit unusual ecological niches and are an interesting source of metabolites with unusual environmental tolerances and of new metabolites for drug screening. In addition, a number of pathogenic organisms thrive under anaerobic conditions and the metabolites they produce are valuable indicators of cell signaling mechanisms, pathogenicity factors, identification markers or indicators for potential drug targets. Thus an efficient method for the production of secondary metabolites, particularly one which allows biofilm formation and differentiation of the culture, is of considerable value to the life sciences industry.

With significant developments in medium optimization strategies for the cultivation of microorganisms under oxygen limiting conditions at high cell density is possible. Organisms previously examined under aerobic conditions may now be screened for the production of natural products that may be induced under oxygen limiting conditions such as surfactin production in *Bacillus subtillus* (Davies at al. 1999)

Recombinant Products

Several industrially important compounds are produced by microorganisms, including both natural and recombinant products. The market for recombinant products for the pharmaceutical as well as other industries has increased in recent years. Recombinant products, including but not limited to enzymes, hormones, antibodies, antibody fragments, virus-like particles, peptides, DNA and RNA fragments are produced by a variety of microbial expression systems. Products may also include chemicals produced by the expression products of recombinant synthetic enzymes.

A variety of expression hosts have been engineered to optimize recombinant product production, solubility and secretion. Expression hosts include a number of bacterial species, fungi, plant cells, insect cells, protozoa and mammalian cells. Most expression systems are aerobic, requiring considerable input of energy to maintain high oxygen mass transfer in submerged culture bioreactors. Most bioprocess technology is focused on obtaining very high cell concentrations in the bioreactor, typically by fed-batch culture mode. High initial substrate concentration and culture fluidity are a major obstacle in achieving high cell density growth. Routinely, once sufficient biomass is present the production host is induced to express the recombinant product of interest. This induction is typically a molecule that is added at the appropriate time, or is a metabolite produced by the production host as a waste product, primary or secondary metabolite. The strategy of producing recombinant proteins once the culture is in the stationary phase is typical since:
1) It allows the production of products that are toxic to the producing organism.
2) Volumetric productivity is improved if the biomass concentration in the reactor is very high.
3) Precursors for the production of the product are typically primary metabolites, which accumulate during the primary growth phase.

It is often difficult to time the addition of recombinant protein inducers optimally so that inducers are added when the culture reaches stationary phase and not too soon or too late. It is particularly difficult when multiple cultures are run in parallel under different conditions during optimization experiments. Thus, "auto-inducing" expression systems have been developed, which have been engineered to switch on recombinant protein expression automatically once the culture has reached stationary phase (Studier, 2005).

Although most recombinant protein expression hosts are aerobic organisms, high density culture is limited because of oxygen mass transfer limitations. Thus, an interest has been shown in developing expression hosts such as lactic acid bacteria (LAB), capable of anaerobic growth.

LAB have been considered to be of major interest as recombinant protein expression hosts. This is due to LAB being Gram positive and therefore more adept to secretion of proteins and less likely to generate immunogenic membrane components that often contaminate the products from Gram negative expression hosts. They are facultative anaerobes, so growth limiting oxygen mass transfer limitations typically experienced in submerged culture are not applicable. Some LAB expression hosts have also been developed with "autoinduction" of recombinant protein expression on onset of stationary phase (Kuipers, et al., 1997; de Vos, 1999). Some examples follow:

1) Induction by Nisin: Nisin is a secondary metabolite and cell signaling molecule produced by the LAB. It is therefore produced when the culture is mature and in stationary phase and will autoregulate the induction of recombinant protein production at the right time. (Xu Xia Zhou et al. 2006)
2) Induction by low pH, lactic acid accumulation and/or onset of stationary phase: The p170 system for the expression of recombinant proteins from *Lactococcus* sp. is induced by the accumulation of lactic acid/lactate, a metabolic waste product which accumulates during the growth phase of LAB, resulting in a drop in pH which could slow down growth sufficiently to induce the onset of the stationary phase. In addition to being induced by an increase in lactic acid/lactate concentration, the system is also induced by the onset of the stationary phase due to nutrient limitation. This system thus autoregulates the induction of protein product expression at the appropriate time. (Madsen et al. 1999)

A problem arises with these systems in batch culture in that the production phase is typically quite short because of a typical over-accumulation of growth inhibiting or toxic metabolic waste products and because excessive nutrient stress kills the culture. Thus, technologies that will allow continuous removal of waste and extension of the stationary phase of at least part of the culture will have a positive impact on the performance of recombinant protein production systems.

The most widely used bacterial expression host, *Escherichia coli* is primarily cultivated in high density cell culture. While the specific growth rate of this organism is highest under aerobic conditions it is able to grow anaerobically. *E. coli* expression systems have been engineered to produce difficult to express, toxic and/or insoluble products. Fermentation technologies allowing for the continuous production and extraction of products that are insoluble at higher concentrations or are toxic to the host organism, offer advantages over traditional submerged fermentation technologies.

DEFINITIONS

Any reference herein to a "microorganism" must be interpreted to mean a reference to organisms which include bacteria and fungi that are capable of growth and metabolism under oxygen-limited or anaerobic conditions.

Any reference herein to a "stationary phase" must be interpreted to mean a period of limited growth or growth and death substantially in equilibrium which typically follows immediately after the primary growth phase in batch cultivation or continuous cultivation of microorganisms.

Any reference herein to "recombinant protein" is synonymous with "recombinant product" and must be interpreted to mean any recombinant product or the product thereof if it is a biosynthetic product, homologous or heterologous to the expression host, the production of which may be induced by some mechanism at the onset of—or during the stationary phase. The product can either be secreted by the expression host into the extracellular environment or retained intracellularly. Recombinant products are not limited to proteins.

Any reference herein to a "nutrient solution" must be interpreted to mean a liquid solution containing one or more nutrients required for microorganism growth and which includes at least one nutrient which is growth limiting. The nutrient solution may also carry an inducer required for initiating the expression of recombinant products.

Any reference herein to an "inducer" must be interpreted to mean a biological or synthetic chemical included in the nutrient solution or a biosynthetic product produced by the immobilised expression host during growth and used as a means of regulating the production of recombinant proteins under the control of a relevant promoter regulating expression of the said recombinant protein.

Any reference herein to "permeate" must be interpreted to mean the spent nutrient solution or product stream that has passed through the biofilm and the substrate and may carry secreted product, metabolic waste products and/or the remainder of nutrients not metabolised by the microorganism during the passage of the nutrient solution through the biofilm.

SUMMARY OF INVENTION

According to one aspect of the invention, there is provided a method of producing secondary metabolites under oxygen-limited or anaerobic culture conditions, which method includes:

providing a porous substrate having a first side and a second side and which has a biofilm of microorganisms attached to the first side thereof, the substrate being configured to allow the passage of secondary metabolites therethrough and to prevent the passage of microorganism cells therethrough; and causing a nutrient solution to flow through the biofilm and the substrate in a direction from the first side thereof to the second side thereof under oxygen-limited or anaerobic culture conditions, at a rate which is sufficiently low for a nutrient gradient to be established across the biofilm wherein the nutrient concentration is relatively higher further from the substrate and sufficiently high to support primary growth of the microorganisms and wherein the nutrient concentration is relatively lower closer to the substrate and sufficiently low to induce and sustain a stationary phase of the microorganisms and thereby cause the microorganisms to produce at least one secondary metabolite, the flow of the nutrient solution through the substrate carrying said secondary metabolite through the substrate to the second side thereof where secreted secondary metabolite can be collected, with the microorganism cells from the biofilm being retained at the first side thereof.

By oxygen-limited or anaerobic conditions is meant conditions where no or substantially no oxygen is present. However, it is envisaged that in certain circumstances the method of the invention may still work if there are low oxygen concentrations present.

The microorganisms may be a substantially pure culture of a strain of a microorganism or a mixed culture of different microorganisms. The microorganisms may be selected from the group consisting of *Clostridium* sp., *Bacillus* sp., *Pseudomonas* sp. *Vibrio* sp., *Rhodopseudomonas* sp., *Desulphovibrio desuffuricans*, and *Candida* sp.

The method of producing the secondary metabolite may be carried out at a temperature within the range of growth and product formation of the microorganisms. The method of producing the secondary metabolite may be carried out at a temperature of 2-109° C., preferably 20-32° C., e.g. 30° C.

The method of producing the secondary metabolite may be carried out at an initial pH within the range of growth and product formation of the microorganisms. The method of producing the secondary metabolite may be carried out at an initial pH of 1-13, preferably 5.5-8.5, e.g. 7.

The method of producing the secondary metabolite may be carried out for a period for as long as the biofilm or culture remains viable and productive and not too dense so as to prevent product flow through the substrate. The method of producing the secondary metabolite may be carried out for a period of 1-30 days, preferably 2-10 days, e.g. 4 days.

The secondary metabolite may be produced intracellularly or extracellularly by the microorganisms. Extracellular metabolites secreted from the biofilm into the nutrient stream and collected in permeate may be sampled and extracted continuously, improving stability and volumetric productivity of such products. Intracellular secondary metabolites may be extracted from biofilms through permeabilisation of cells, osmotic shock or cell lysis procedures. Extracted intracellular products may be separated from treated biomass by filtering the extract through the substrate from the first side to the second side by the same means as the nutrient solution is supplied to the biofilm and permeate removed from the bioreactor. High cell density of biofilm cultures ensures high yields of biomass associated metabolites.

It will be appreciated that biofilm thickness is dependent on the nutrient content of the nutrient solution and type of microorganism cultured. The biofilm should be of sufficient thickness to establish a nutrient gradient across the biofilm such that part of the biofilm experiences nutrient starvation and enters and sustains stationary phase growth and secondary metabolite production. The biofilm may have a thickness of 0.1-10 mm, preferably 0.1-4 mm, e.g. 3 mm.

Flow rate of the nutrient solution from the first side to the second side, through the biofilm and the substrate should be such that the microorganism remains immobilized and the optimal volumetric productivity of secondary metabolite production is maintained. The flow rates may be 0.01-10 volumes nutrient solution per bioreactor volume.

According to another aspect of the invention there is provided apparatus for producing a secondary metabolite under oxygen-limited or anaerobic conditions, which apparatus includes at least one porous substrate having a first side and a second side; and a feeding arrangement for feeding a nutrient solution under oxygen-limited or anaerobic culture conditions into contact with microorganisms which become attached and form, in use, in a biofilm on the first side of the substrate, the feeding arrangement being operable to cause the nutrient solution to flow through the biofilm and the substrate in a direction from the first side thereof to the second side thereof at a rate sufficiently low for a nutrient gradient to be established across the biofilm wherein the nutrient concentration is relatively higher further from the substrate and being sufficiently high to support primary growth of the microorganisms and wherein the nutrient concentration is relatively lower closer to the substrate and sufficiently low to induce and sustain a stationary phase of the microorganisms thereby to cause the microorganisms to produce a secondary metabolite product, the substrate being configured to allow the passage of product-containing nutrient solution through the substrate to the second side thereof and to prevent the passage of microorganism cells from the biofilm through the substrate.

The feeding arrangement may include at least one of a mechanical source and a pneumatic source of compressed air, for feeding the nutrient solution into contact with the biofilm and causing the nutrient solution to flow through the biofilm and the substrate.

The apparatus may include a permeate collection means for collecting permeate from the second side of the substrate.

The substrate may comprise a porous membrane having apertures sufficiently large to permit passage of product-containing nutrient solution therethrough, but which apertures are sufficiently small to prevent the passage of microorganism cells therethrough. The exact configuration of the membrane may vary greatly. In particular embodiments, the membrane may be in the form of a hollow-fibre membrane, a capillary membrane or may have a tubular or flat sheet configuration.

The apparatus may include a housing for the porous substrate, the housing being spatially separate from the porous substrate. The housing may include an inlet for the nutrient solution and an outlet for discharging permeate from the housing.

According to a further aspect of the invention, there is provided a method of producing at least one recombinant product under oxygen-limited or anaerobic culture conditions, which method includes:

providing a porous substrate having a first side and a second side and which has a biofilm of microorganisms attached to the first side thereof, the substrate being configured to allow the passage of recombinant product therethrough and to prevent the passage of microorganism cells therethrough; and causing a nutrient solution to flow through the biofilm and the substrate in a direction from the first side thereof to the second side thereof under oxygen-limited or anaerobic culture conditions, at a rate which is sufficiently low for a nutrient gradient, having a concentration differential, to be established across the biofilm wherein the nutrient concentration is relatively higher further from the substrate and sufficiently high to support primary growth of the microorganisms and wherein the nutrient concentration is relatively lower closer to the substrate and sufficiently low to enter and sustain a stationary phase of the microorganisms thereby to induce production of at least one recombinant product by the microorganisms, the flow of the nutrient solution through the substrate carrying the recombinant product through the substrate to the second side thereof where the recombinant product can be collected, with microorganism cells from the biofilm being retained at the first side thereof.

By oxygen-limited or anaerobic conditions is meant conditions where no or substantially no, oxygen is present during stationary phase growth. However, it is envisaged that in certain circumstances the method of the invention may still work if low concentrations of oxygen are present.

Induction may be caused in various ways such as by nutrient depletion, addition of an inducer molecule, accumulation of a primary metabolic product or secondary metabolite produced under nutrient limiting conditions, auto-induction, or the like. In other words, the method may use derepression and/or induction of recombinant gene expression. The induction may occur through the addition of an inducer molecule to the nutrient solution or through the accumulation of a primary metabolic product or secondary metabolite produced under nutrient limiting conditions, such that the flow of the nutrient solution through the substrate and biofilm carries said inducer through the biofilm from the first side to the second side, thereby to induce production of said recombinant product by the microorganisms.

The inducer may be any suitable molecule such as L-arabinose (0.00002-2%), isopropyl b-D-thiogalacto-side (IPTG)

(0.1-1 mM) or methanol (0.5-1.5%) that interacts with a specific promoter with which a recombinant expression system is engineered. Concentration of inducer may be varied in order to optimize the expression of soluble, correctly folded recombinant or protein products.

The microorganisms may be a substantially pure culture of a strain of a microorganism or a mixed culture of different microorganisms. The microorganisms may be selected from the group consisting of but not limited to *Lactococcus lactis, Escherichia coli, Bacillus subtillus, Pichia* sp., *Candida* sp., *Hansenula polymorphs* and *Saccharomyces cerevisiae*.

The method of producing the recombinant product may be carried out at a temperature within the range of growth and product formation of the microorganism. The method of producing the recombinant product may be carried out at a temperature of 2-109° C., preferably 20-40° C., e.g. 30° C.

For *Lactococcus lactis* cultures, the method may be carried out at a temperature of 25-32° C. Optimal growth temperature is 30° C. However lower growth temperatures such as 25° C. are growth limiting and may extend the duration of recombinant product production process.

For *Escherichia coli* cultures, the method may be carried out at a temperature of 30-40° C. Optimal growth temperature is 37° C. However lower growth temperatures such as 30° C. are growth limiting and may be used to extend the duration of the recombinant product production process.

The method of producing the recombinant product may be carried out at an initial pH within the range of growth and product formation of the microorganism. The method of producing the recombinant product may be carried out at an initial pH of 1-13, preferably 5.5-8.5, e.g. 7.

For *Lactococcus lactis* cultures, the method may be carried out at an initial pH of 5.5-8.5.

For *Escherichia coli* cultures, the method may be carried out at an initial pH of 5.5-8.5.

The method of producing the recombinant product may be carried out for a period for as long as the biofilm or culture remains viable and productive and not too dense so as to prevent product flow through the substrate. The method of producing the recombinant product may be carried out for a period of 1-30 days, preferably 2-10 days, e.g. 4 days.

For *Lactococcus lactis*, the method may be carried out for a period of 4 days.

For *Escherichia coli*, the method may be carried out for a period of 1 day.

The recombinant product may be produced intracellularly or extracellularly by the microorganisms. The recombinant product may be collected from the first side if secreted by the microorganisms or may be harvested from the biofilm if retained intracellularly by the microorganisms. Intracellular metabolites may be retained within the cytoplasm or secreted to the periplasmic space and extracted using cell lysis or cell permeabilisation procedures such as osmotic shock.

Nutrient solution may be passed through the biofilm and substrate at a flow rate that is sufficient to sustain and immobilise the microorganism while maintaining a nutrient gradient across the biofilm. Flow rates may differ depending on the nutrient content of the nutrient solution and or the type of microorganism cultured. Flow rates may range from 0.001-10 volumes nutrient solution per reactor volume per hour.

Biofilm thickness may depend on the nutrient content of the nutrient solution and the type of microorganism cultured. The biofilm may have a thickness of 0.1-10 mm e.g. 1-3 mm for *L. lactis*, and should be limited such that the flow rate of the nutrient solution is maintained within a suitable range for the biofilm or culture to remain viable and productive and not too thick so as to prevent product flow through the substrate.

According to another aspect of the invention there is provided apparatus for producing a recombinant product under oxygen-limited or anaerobic conditions, which apparatus includes:

at least one porous substrate having a first side and a second side; and a feeding arrangement for supplying a nutrient solution under oxygen-limited or anaerobic culture conditions in contact with microorganisms which become attached and form, in use, a biofilm on the first side of the substrate, the feeding arrangement being operable to cause the nutrient solution to flow through the biofilm and the substrate in a direction from the first side thereof to the second side thereof at a rate sufficiently low for a nutrient gradient to be established across the biofilm wherein the nutrient concentration is relatively higher further from the substrate and sufficiently high to support primary growth of the microorganisms and wherein the nutrient concentration is relatively lower closer to the substrate and sufficiently low to induce and sustain a stationary phase of the microorganisms thereby to induce production of at least one recombinant product by the microorganisms, the substrate being configured to allow the passage of product-containing nutrient solution through the substrate to the second side thereof and to prevent the passage of microorganism cells from biofilm at the first side through the substrate to the second side.

The feeding arrangement may include at least one mechanical and pneumatic source such as compressed air, for feeding the nutrient solution into contact with the biofilm and causing the nutrient solution to flow through the biofilm and the substrate.

The apparatus may include product collection means for collecting the product from the second side of the substrate.

The substrate may comprise a porous membrane having apertures sufficiently large to permit the flow of product and nutrient solution therethrough, but which apertures are sufficiently small to prevent the transfer or passage of microorganism cells therethrough. The exact configuration of the membrane may vary greatly. In particular embodiments, the membrane may be in the form of a hollow-fibre membrane, a capillary membrane or may have a tubular or flat sheet configuration.

The apparatus may include a housing for the porous substrate, the housing being spatially separated from the porous substrate. The housing may include an inlet for the nutrient solution and an outlet for discharging permeate from the housing.

Unless otherwise defined, all technical and scientific terms used herein have the same meaning as commonly understood by one of ordinary skill in the art to which this invention pertains. In case of conflict, the present document, including definitions, will override terms commonly understood by one of ordinary skill in the art. Preferred methods and apparatus are described below, although methods and apparatus similar or equivalent to those described herein can be used in the practice or testing of the present invention. All publications, patent applications, patents and other references mentioned herein are incorporated by reference in their entirety. The methods, apparatus and examples disclosed herein are for illustrative purposes only and not intended to be limiting.

BRIEF DESCRIPTION OF DRAWINGS

Further features of the invention are described hereinafter by way of a non-limiting example of the invention, with reference to and as illustrated in the accompanying diagrammatic drawings. In the drawings.

DESCRIPTION OF PREFERRED EMBODIMENTS

Secondary Metabolites

Figure 1:
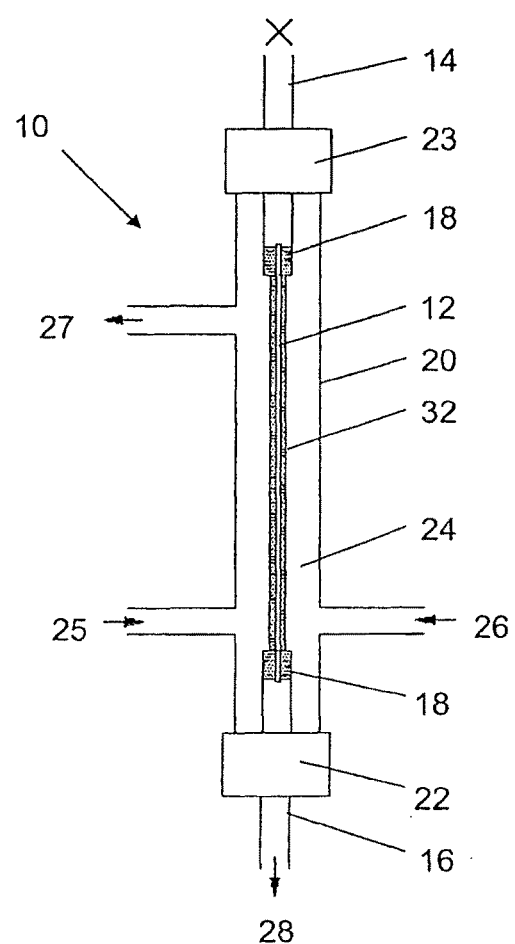
FIG. 1 shows a schematic side elevation of an apparatus in accordance with the invention.

With reference to FIGS. 1 to 4 of the drawings, an apparatus for producing a secondary metabolite under oxygen limited or anaerobic conditions, in accordance with the invention, is designated generally by the reference numeral 10. The apparatus is in the form of a bioreactor 10 shown in FIG. 1 of the drawings at a laboratory scale, however, it will be appreciated that the principles embodied in the bioreactor can be applied to an up-scaled or commercial embodiment.

The bioreactor 10 includes a ceramic hollow fibre capillary membrane 12 with ends of the membrane being potted into plastic inserts 14, 16 with epoxy 18, comprising a ceramic insert. It should be appreciated that other resins or mechanical seals may also be used. A housing or reactor shell 20 of glass is arranged coaxially with the capillary membrane 12 and is provided with end caps 22 and 23 which screw onto the glass housing 20. The housing 20 includes a feed inlet 26 for introducing a liquid nutrient feed solution for microorganisms into the space 24 between the porous substrate and the housing and an inoculation inlet 25 for introducing an inoculum into the housing for attachment to the membrane 12. The housing further includes a feed outlet 27 for discharging the feed solution from the housing. The ceramic insert 12, 14, 16 includes a product outlet 28 for discharging permeates from the housing.

In use, a biofilm 32 is established on an external surface 30 of the capillary membrane 12. This is achieved by filtering a spore or vegetative inoculum of a desired microorganism through the capillary membrane 12 and draining any permeate out of the lumen 34 and through the outlet 28. The lumen 34 is thus in flow communication with the outlet 28. The inoculum is thus immobilised on the membrane surface 30. The membrane 12 has a relatively thin, porous skin 36 on the inside and a relatively thick, finger-like, externally unskinned void structure 38 radiating outwardly from the skin 36. Typically, the membrane 12 has an outside diameter of about 2 mm.

Figure 2:
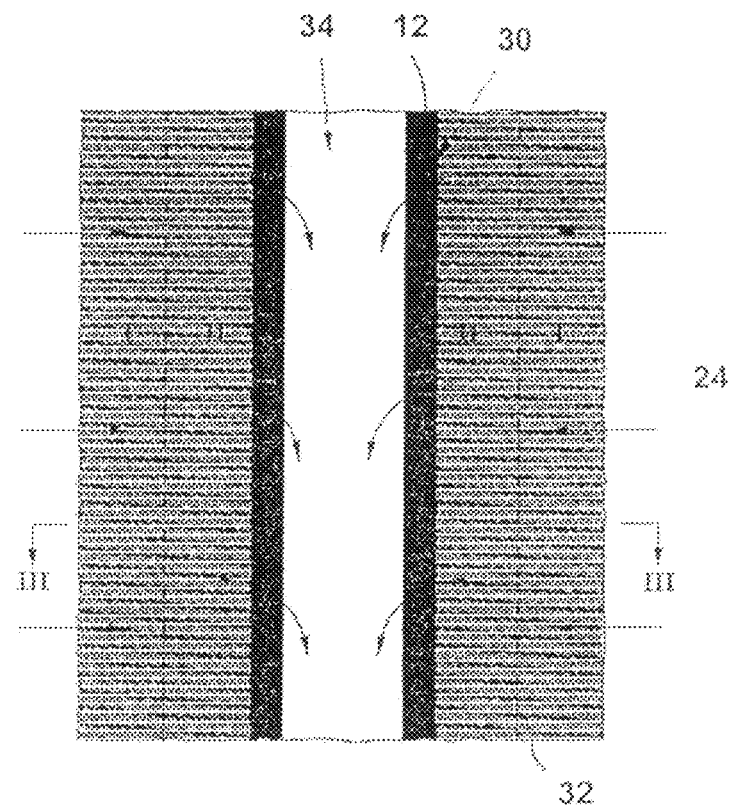
FIG. 2 shows a schematic side elevation of a portion of a porous substrate of the apparatus of FIG. 1, coated on an outer side thereof with a biofilm, and illustrating a nutrient solution flow regime through the biofilm.
Figure 3:
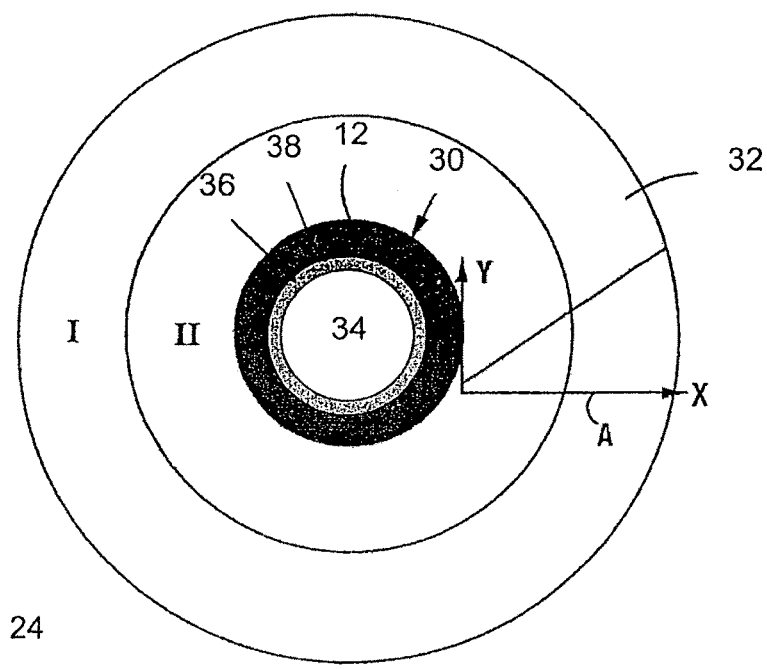
FIG. 3 shows a schematic sectional plan view of the porous substrate of FIG. 2, sectioned along section line III-III of FIG. 2.

Appropriate nutrient solution for the microorganism is introduced into the housing via the nutrient inlet 26. The nutrient solution is caused to flow through the membrane 12 in a direction from the outer side of the membrane to the inner side thereof. Fundamental to the production of secondary metabolites is the concept of nutrient starvation which stresses the microorganism and thus controls the production of secondary metabolites. This is achieved with the membrane-immobilised biofilm bioreactor 10 by the production of radial nutrient concentration gradients through the biofilm 32. As a result, the nutrient concentration at the exposed outer surface of the biofilm 32 is high, whereas the nutrient concentration at the membrane/biofilm interface 30 is low. In FIGS. 2 and 3 of the drawings, for the purposes of illustration, a high nutrient concentration zone is designated by the reference number I and a low nutrient concentration zone is designated by the reference numeral II. In zone I the nutrient concentration is sufficiently high to support primary growth of the microorganisms, while in zone II the nutrient concentration is sufficiently low to cause nutrient starvation which stresses the microorganisms thereby to induce and sustain a stationary phase of the microorganisms. A biofilm population of growing and reproducing cells is established at the exposed outer surface of the membrane, whereas secondary metabolites are produced for extended periods in zone II of the biofilm. In FIG. 3, a graph "A" depicts the nutrient concentration level (y axis) vs. distance from the membrane surface (x axis).

The porosity of the membrane 12 is such that secondary metabolites are allowed to pass through the membrane into the lumen 34, whereas the cells of microorganisms are prevented from passing through the membrane. As a result, secondary metabolites produced in zone II of the biofilm are carried inwards into the lumen 34 of the membrane by the flow of the nutrient solution from an outer side of the membrane into the lumen 34. The liquid growth medium is forced under pressure through the membrane 12 using a pneumatic source such as compressed air or a mechanical source such as a pump or a combination of compressed air and a pump. As new biomass is laid down due to the growth of the culture in the nutrient solution, the biofilm increases in thickness until part of the biofilm is starved and the nutrient gradient described hereinabove is established. The process allows the production of secondary metabolites for an extended period. This period ends when lysis of dead cells releases contaminants or when the biofilm resistance is too high to allow for penetration of the membrane 12 by the growth medium.

Figure 4A:
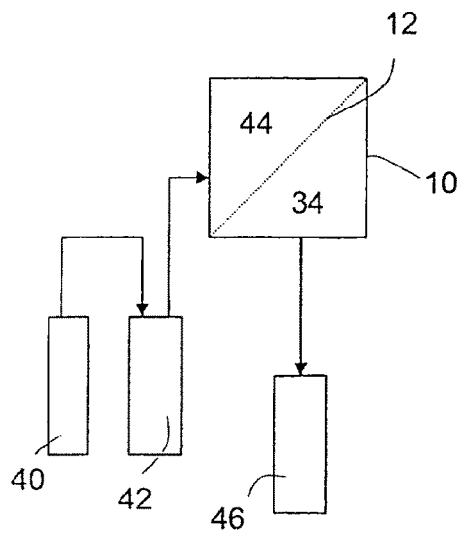
FIGS. 4A-4D show schematic block diagrams illustrating different fluid flow regime options for the supply of a nutrient solution to the apparatus of FIG. 1 and for the collection of product therefrom.

With reference to FIG. 4A of the drawings, a typical fluid flow regime where a pneumatic source 40 such as compressed air is used to pressurize the nutrient solution contained in a reservoir 42 for feeding the nutrient solution under pressure into the extra-capillary space 44 defined between the housing of the bioreactor 10 and the membrane 12. After passing through the membrane 12, the product-containing nutrient solution is collected in a product collection vessel 46.

Figure 4B:
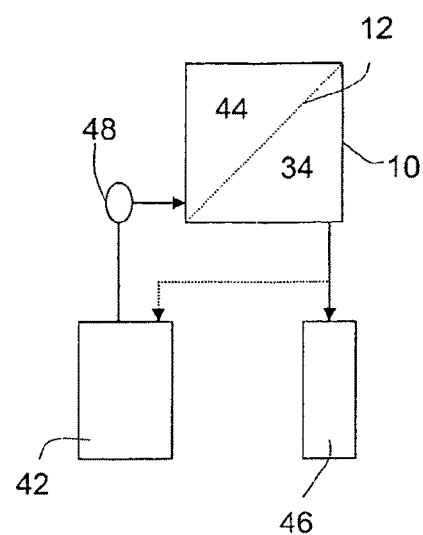

With reference to FIG. 4B, a mechanical source 48 is used to pump the nutrient solution into the extra-capillary space 44. After passing through the bioreactor, the product is separated from the product-containing nutrient solution which is returned to the reservoir 42. The separated product is collected in the product collection vessel 46.

Figure 4C:
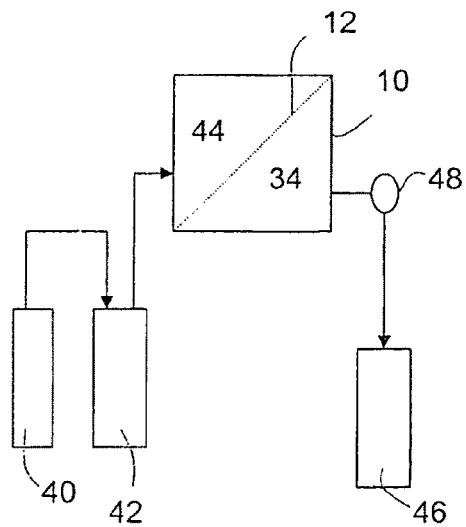

With reference to FIG. 4C, a pneumatic source 40 and a mechanical source 48 is used in combination to feed the nutrient solution into the bioreactor and to extract the product-containing nutrient solution there from. The pneumatic source 40 is positioned upstream of the bioreactor for feeding nutrient solution into the extra-capillary space 44 and the mechanical source is located downstream of the bioreactor and operates as a suction or vacuum pump for extracting product-containing nutrient solution from the lumen 34, which is collected in the product collection vessel 46.

Figure 4D:
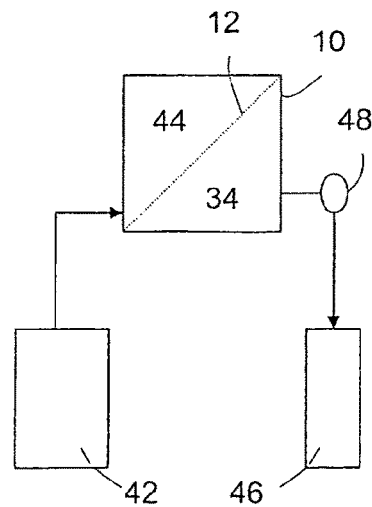

The fluid flow regime shown in FIG. 4D is similar to the fluid flow regime depicted in FIG. 4C, with the only difference being that the pneumatic source is not used.

It will be appreciated that the exact configuration of the bioreactor and of the fluid flow regime may vary greatly while still incorporating the essential features defined hereinabove.

The bioreactor in accordance with the invention, allows for a high mass transfer of nutrients to microorganism cells because of the convective flow of the liquid nutrient solution through the membrane. This flow also provides for the rapid removal of secreted product from the bioreactor while preventing any reverse flow of secreted product back through the membrane. Due to the fact that product is removed soon after production there is minimal product loss due to decay. The bioreactor requires no mechanical agitation which may damage microorganism cells. As a result, the microorganism culture in the bioreactor 10 is more productive and product decay is reduced. Also, no foaming occurs, obviating the need for anti-foaming agents and allowing for a greater proportion of the reactor capacity to be used. As biomass is retained in the reactor, unit operations are reduced since harvesting is not required and the product is of a relatively high purity. The bioreactor allows a relatively high cell density per unit volume resulting in higher volumetric productivity of both intracellular and extracellular products. When operated, the bioreactor allows for the extended production of secreted secondary metabolites or high yield biomass associated intracellular metabolites.

The concentration of metabolic waste product increases as the nutrient solution perfuses the biofilm, which may also regulate product formation in cultures where the accumulation of metabolic waste induces secondary metabolite production.

Example 1

*Bacillus subtillus* ATCC 21332

Surfactin Production Under Oxygen Limited Conditions

Surfactin is a lipopeptide-like biosurfactant produced by various strains of *B. subtillus*. Biosurfactants commonly have the advantage of biodegradability, reduced toxicity and biocompatibility over chemically synthesized surfactants and retain their function at extremes of temperature, pH and salinity (Georgiou et al, 1992). Surfactin also exhibits antimicrobial (Vollenbrioch et al 1997a), antiviral (Vollenbrioch et al 1997b), fibrin clotting inhibition (Bernheimer et al 1970) and anti-inflammatory properties.

*B. subtillus* is commonly described as a strict aerobe but it has also been reported that anaerobic growth is possible (Nakano et al 1999; Davis et al 1999). In addition, levels of surfactin production have been shown to be enhanced under oxygen limiting growth conditions (Davis et al 1999). Improved bioreactor and process design for surfactin production have also developed, primarily through medium optimization (Cooper et al 1981; Wei and Chu 1998; Davis et al 1999; Wei et al 2003; Wei et al 2004), high cell density culture and the concentration and extraction of surfactin from fermentors in foam (Davis at al 2001; Yeh et al 2006).

Addition of ammonium nitrate to growth medium improved biomass yields under oxygen limiting conditions and was shown to enhance surfactin production (Davis et al 1999). Improved buffering capacity of growth medium (Wei et al 2003), $MgSO_4$ and $FeSO_4$ (Cooper et al 1981; Wei et al 2004) were also shown to improve surfactin yields (Wei and Chu 1998; Wei et al 2003).

Sterilisation:

Bioreactors were autoclaved and set up for anaerobic operation according to standard operating procedures (SOPs). Filter sterilized medium was aseptically dispensed into each of medium supply vessels prior to starting the experiment.

Inoculation:

Bioreactors were each inoculated with 3 ml of *B. subtillus* ATCC pre-inoculum, cultured in Nutrient Broth (Merck) at 30° C. for 24 hrs. Inoculum was aseptically injected directly into the extracapillary space (ECS) of each bioreactor according to SOP.

Operation:

Bioreactors were manifolded into banks in which medium supply was regulated using a single source of compressed air. Each 20 ml bioreactor within a given bank was supplied with nutrients from its own medium supply vessel. Within each bank, replicate bioreactors were supplied with either mineral salts medium (Cooper et al. 1991) or iron-enriched mineral salts medium (Wei et al. 2003).

Following inoculation medium was supplied to each bioreactor at 5 kPa. Pressures were adjusted at intervals in order to maintain pH of permeate above pH 6.

Analysis

Bioreactors were sampled periodically and volumes and pH recorded. pH of samples was adjusted to ~pH 2 using concentrated HCl in order to precipitate and concentrate surfactin before centrifuging at 4000 rpm for 10 min at 4° C. Supernatant was decanted and the pellet resuspended in 1:20 vol. Abs Ethanol. Concentrate was transferred to a microfuge tube and centrifuged at 14 000 rpm using a microfuge prior to analysis.

Surfactin concentration was measured by reverse phase HPLC (waters: separations module 2695, PDA 2696) equipped with an Xterra C18 column (5 µm, 3.9 mm×150 mm). The mobile phase consisted of 30% 3.8 mM trifluoroacetic acid and 70% acetonitrile. All solvents were HPLC grade. Sample size was 50 µl and the elution rate was 1 ml/min. Absorbance of the eluent was monitored at 205 nm. Surfactin was calculated from Fluke (Cat. 86196). Calculation of surfactin concentration was based on 8 major peaks identified in the standard (see FIG. 5A).

Productivity

*B. subtillis* growth and surfactin production in bioreactors using growth medium published for optimal surfactin production was hampered by precipitation of the growth medium over time. Precipitation of medium components was more pronounced in growth medium containing increased levels of $FeSO_4$ (Wei et al. 2006). Precipitation resulted in reduced pH of the nutrient solution, inhibition of growth of the microorganism and the formation of insoluble surfactin.

Figure 5A:
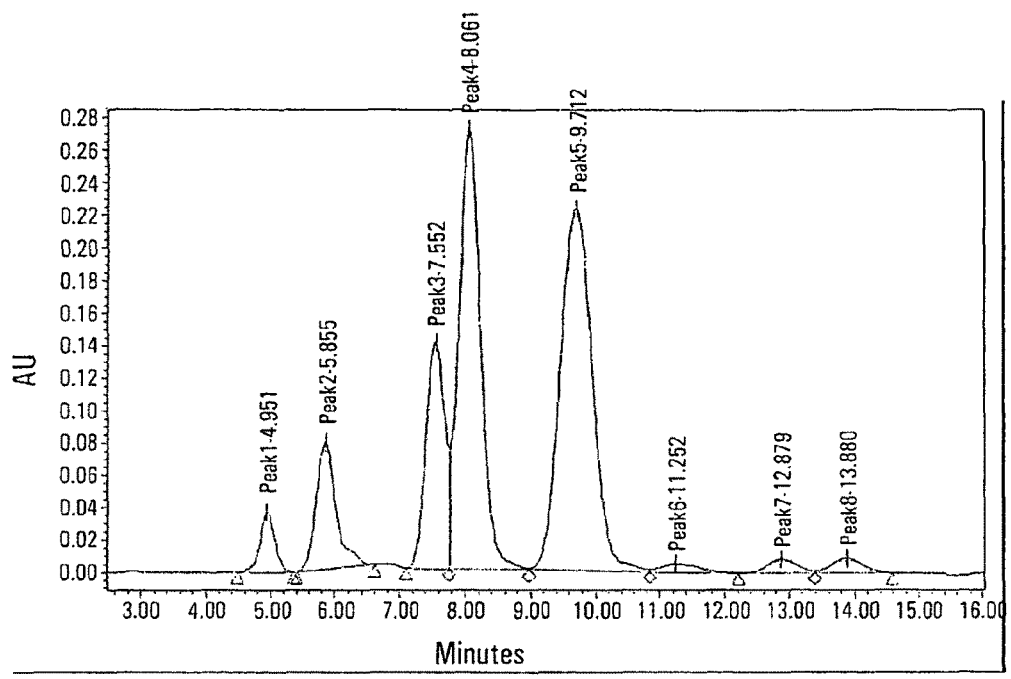
FIGS. 5A and 5B are HPLC chromatograms showing separation of surfactin isomers detected in the Fluka surfactin standard (A) and in a typical sample produced by *Bacillus subtillis* under oxygen limiting conditions using a single fibre membrane bioreactor (B)
Figure 5B:
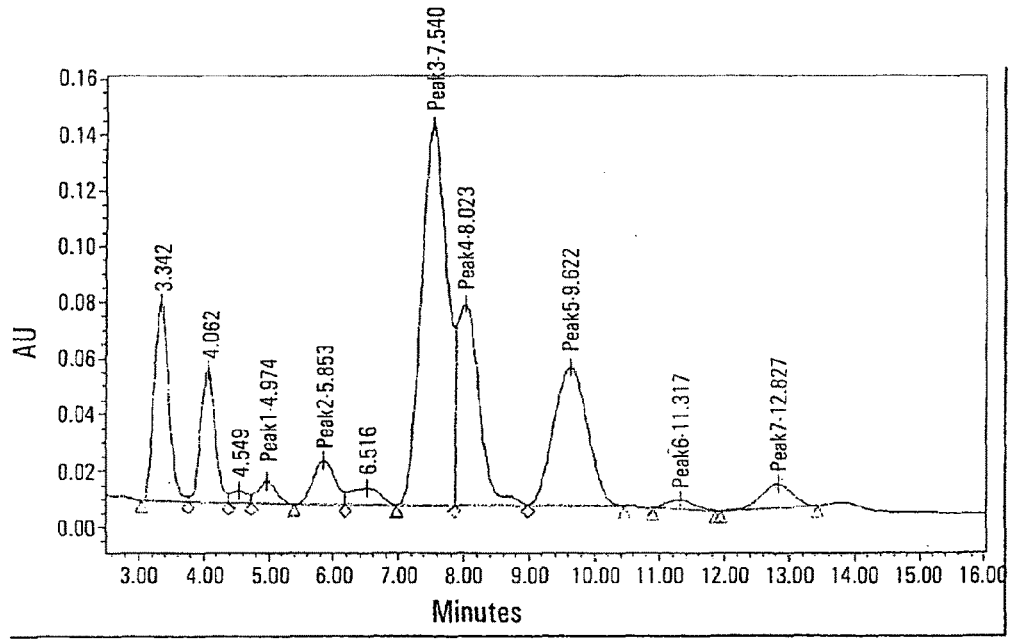

With reference to FIG. 5B, showing a typical HPLC chromatogram for surfactin produced by *B. subtillis* ATCC 21332 cultured in a 20 ml bioreactor. While all eight major peaks were identified in the sample, the ratio of these peaks differed from that observed in the standard (FIG. 5A). In addition to the eight peaks identified in the Fluka standard, two additional major peaks not present in the standard were observed (not identified) in samples (FIG. 5 B).

Surfactin production in iron-enriched growth medium was negligible. Increased precipitation of nutrients was observed over time in this medium with resultant pH of below 5, inhibiting growth of the microorganism. By changing the growth medium to Cooper's mineral salt medium pH was recovered and growth and surfactin production improved (data not shown).

Table 1 lists the productivity of bioreactors cultured using Cooper's mineral salts medium. Higher surfactin levels were correlated with increased flow rate and higher pH levels. Surfactin precipitates in solutions below pH 6. Further medium optimization is required to maximize anaerobic growth of *B. subtillis*, optimize surfactin production and prevent medium precipitation.

TABLE 1

Surfactin production in bioreactors cultured using Cooper's mineral salts medium (n = 2)

| | Time (hrs) | | | | | |
|---|---|---|---|---|---|---|
| | 31 | 46 | 53 | 59 | 70 | 76 |
| kPa | 5 | 5 | 5 | 10 | 10 | 10 |
| pH | 6.7 | 6.7 | 6.3 | 6.0 | 6.0 | 6.0 |
| Permeate vol. (ml) | 133 | 159 | 22 | 26 | 36 | 19 |
| Flux | 19 | 11 | 3 | 4 | 3 | 3 |
| Surfactin conc (µg/ml) | 18.480 | 14.500 | 5.000 | 0.260 | 0.080 | 0.300 |
| Total Surfactin (mg) | 2.4551 | 2.2813 | 0.1100 | 0.0066 | 0.0014 | 0.0057 |

Recombinant Products:

With reference to FIGS. 1 to 4 of the drawings, an apparatus for producing a recombinant protein under oxygen limited or anaerobic culture conditions, in accordance with the invention, is designated generally by the reference numeral 10. The apparatus is in the form of a bioreactor 10 shown in FIG. 1 of the drawings at a laboratory scale, however, it will be appreciated that the principles embodied in the bioreactor can be applied to a scaled up or commercial embodiment.

The bioreactor 10 includes a ceramic hollow fibre capillary membrane 12 with ends of the membrane being potted into plastic inserts 14, 16 with epoxy 18, comprising a ceramic insert. It should be appreciated that alternative resins or mechanical sealing technology may also be used. A housing or reactor shell 20 of glass is arranged coaxially with the capillary membrane 12 and is provided with end caps 22 and 23 which thread onto the glass housing 20. The housing 20 includes a feed inlet 26 for introducing a liquid nutrient feed solution for microorganisms into the space 24 between the porous substrate and the housing and an inoculation inlet 25 for introducing an inoculum into the housing for attachment to the membrane 12. The housing further includes a feed outlet 27 for discharging the feed solution from the housing. The ceramic insert 12, 14, 16 includes a product outlet 28 in fluid communication with the capillary lumen 34 for discharging permeate from the housing.

In use, a biofilm 32 is established on an external surface 30 of the capillary membrane 12. This is achieved by filtering a spore or vegetative inoculum of the desired microorganism through the capillary membrane 12 and draining any permeate out of the lumen 34 and through the outlet 28. The lumen 34 is thus in flow communication with the outlet 28. The inoculum is thus immobilised on the membrane surface 30. The membrane 12 has a relatively thin, porous skin 36 on the inside and a relatively thick, finger-like, externally unskinned void structure 38 radiating outwardly from the skin 36. Typically, the membrane 12 has but is not limited to an outside diameter of about 3 mm.

Appropriate nutrient solution for the microorganism is introduced into the housing via the nutrient inlet 26. The nutrient solution is caused to flow through the membrane 12 in a direction from the outer side of the membrane to the inner side thereof. Fundamental to the production of recombinant proteins is the concept of induction or nutrient starvation which regulates gene expression and thus controls the production of recombinant proteins. This is achieved with the membrane-immobilised biofilm bioreactor 10 by the production of radial nutrient concentration gradients through the biofilm 32. As a result, the nutrient concentration at the exposed outer surface of the biofilm 32 is high, whereas the nutrient concentration at the membrane/biofilm interface 30 is low. In FIGS. 2 and 3 of the drawings, for the purposes of illustration, a high nutrient concentration zone is designated by the zone reference number I and a low nutrient concentration zone is designated by the zone reference numeral II. In zone I the nutrient concentration is sufficiently high to support primary growth of the microorganisms, while in zone II the nutrient concentration is sufficiently low to cause nutrient starvation which stresses the microorganisms thereby to enter and sustain a stationary phase of the microorganism, and the level of inducer molecule is sufficiently high to induce recombinant protein production. A biofilm population of growing and reproducing cells is established at the exposed outer surface of the membrane, whereas recombinant proteins are produced for extended periods in zone II of the biofilm. In FIG. 3, a graph "A" depicts the nutrient concentration level (y axis) vs. distance from the membrane surface (x axis).

The porosity of the membrane 12 is such that recombinant proteins are allowed to pass through the membrane into the lumen 34, whereas the cells of microorganisms are prevented from passing through the membrane. As a result, recombinant proteins produced in zone II of the biofilm are carried inwards into the lumen 34 of the membrane by the flow of the nutrient solution from a first side of the membrane into the lumen 34 or second side of the membrane. The liquid growth medium is forced pneumatically under pressure through the membrane 12 using compressed air (or another suitable gas) or mechanically using a pump or a combination of compressed air and a pump. As new biomass is laid down due to the growth of the culture in the nutrient solution, the biofilm increases in thickness until part of the biofilm is starved and the nutrient gradient described hereinabove is established. The process allows the production of recombinant proteins for an extended period. This period ends when lysis of dead cells releases contaminants or when the biofilm resistance becomes too high to allow for penetration of the membrane 12 by the growth medium.

With reference to FIG. 4A of the drawings, a typical fluid flow regime using a pneumatic source 40 such as compressed air, is used to pressurize the nutrient solution contained in a reservoir 42 for feeding the nutrient solution under pressure into the extra-capillary space 44 defined between the housing of the bioreactor 10 and the membrane 12. After passing through the membrane 12, the permeate is collected in a product collection vessel 46.

With reference to FIG. 4B, mechanical source such as a pump 48 is used to pressurize the nutrient solution into the extra-capillary space 44. After passing through the bioreactor, the product is separated from the product-containing nutrient solution which is returned to the reservoir 42. The permeate is collected in the product collection vessel 46.

With reference to FIG. 4C, a pneumatic source 40 such as compressed air and a mechanical source 48 such as a pump is used in combination to feed the nutrient solution into the bioreactor and to extract the product-containing permeate there from. The pneumatic source 40 is positioned upstream of the bioreactor for feeding nutrient solution into the extracapillary space 44 and the pump is located downstream of the bioreactor and operates as a suction or vacuum pump for extracting permeate from the lumen 34, which is collected in the product collection vessel 46.

The fluid flow regime shown in FIG. 4D is similar to the fluid flow regime depicted in FIG. 4C, with the only difference being that the pressurized gas source is not used.

It will be appreciated that the exact configuration of the bioreactor and of the fluid flow regime may vary greatly while still incorporating the essential features defined hereinabove.

The bioreactor in accordance with the invention, allows for a high mass transfer of nutrients to microorganism cells because of the convective flow of the liquid nutrient solution through the biofilm and substrate. This flow also provides for the rapid removal of product from the bioreactor while preventing any reverse flow of product back through the membrane. Due to the fact that product is removed soon after production, there is minimal product loss due to decay. The bioreactor requires no mechanical agitation which may damage microorganism cells. As a result, the microorganism culture in the bioreactor 10 is more productive and product decay is reduced. Also, no foaming occurs, obviating the need for anti-foaming agents and allowing for a greater proportion of the reactor capacity to be used. As biomass is retained in the reactor, unit operations are reduced since harvesting is not required and the product is of a relatively high purity. The bioreactor allows a relatively high cell density per unit volume resulting in higher volumetric productivity. When operated, the bioreactor allows for the extended production of recombinant proteins.

The concentration of metabolic waste products increases as the nutrient solution perfuses the biofilm, which may also induce product formation in cultures where the accumulation of metabolic waste regulates gene expression. It will be appreciated that after the establishment of the nutrient gradient, product formation may be induced by low pH and organic acid accumulation.

Example 2

*Lactococcus lactis* P170 Expression System (Bioneer)

The *L. lactis* P170 expression system is an auto-inducible expression system that is induced under glucose-limiting growth conditions and with the accumulation of lactic acid, produced by the organism, within the growth environment. Optimal pH for induction is between pH 5.5-6.5. Product is secreted.

*L. lactis* strain PRA290, engineered to produce β-lactamase under the control of P170, was used in this example. β-lactamase activity in permeate was quantified spectrophotometrically using a 96-well microtitre plate procedure based on the Nitrocefin method (Oxoid).

Sterilisation:

Bioreactors 10 were autoclaved and set up for anaerobic operation according to standard operating procedures (SOPs). Filter sterilized medium was dispensed aseptically into each of the medium supply vessels prior to starting the experiment.

Inoculation:

Bioreactors 10 were each inoculated with 1 ml of *L. lactis* PRA290 (β-lactamase producing) pre-inoculum, cultured in M17-G5 growth medium (Oxoid) at 30° C. for 16 hrs. Inoculum was injected directly into the extracapillary space (ECS) of each bioreactor according to SOP.

Operation:

Bioreactors 10 were manifolded into banks in which medium supply was regulated using a single source of compressed air. Each bioreactor within a given bank was supplied with nutrients from its own medium supply vessel. Within each bank, replicate bioreactors were supplied with either LM5-V100-G75 containing either 200 mM or 400 mM potassium phosphate buffer (pH 7.2). Flux, pH and β-lactamase activity were assessed on fresh samples.

Following inoculation, medium was supplied to each SFR at 8 kPa overnight. Pressures were adjusted as follows:

TABLE 2

| Time post-inoculation (hrs) | Pressure (kPa) |
| --- | --- |
| 0 | 8 |
| 16 | 13 |
| 22 | 18 |
| 28 | 30 |
| 30 | 50 |
| 34 | 70 |
| 36 | 80 |

Productivity

Figure 6A:
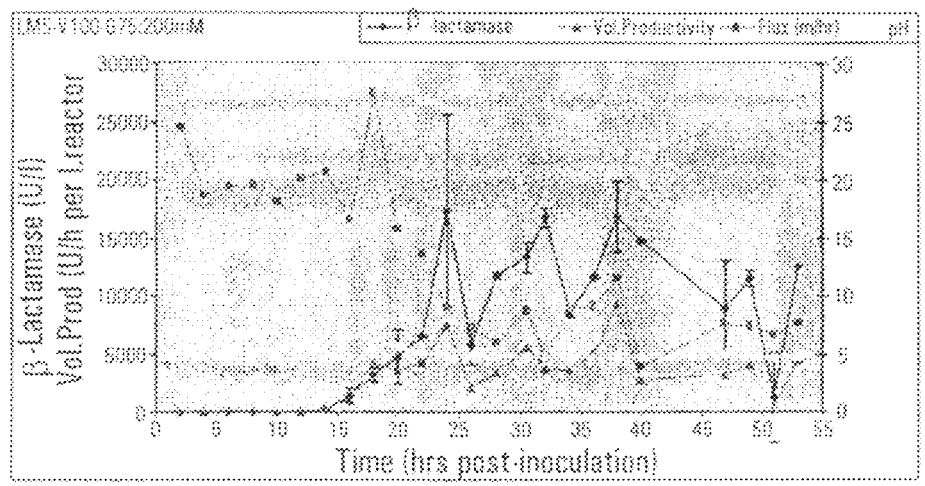
FIGS. 6A and 6B show graphs of β-lactamase production by *L. lactis* PRA290 using the apparatus of FIG. 1. Bioreactors were operated using a nutrient solution containing either 200 mM sodium phosphate buffer (A) or 400 mM sodium phosphate buffer (B)
Figure 6B:
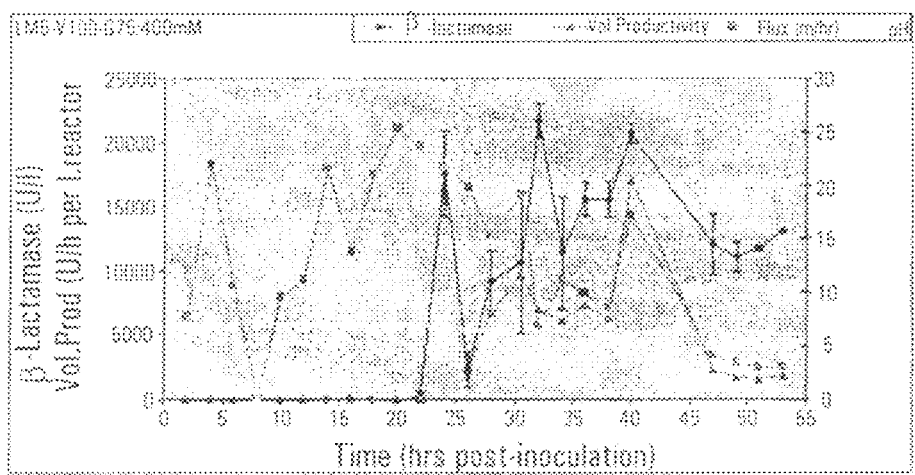

With reference to FIGS. 6A and 6B of the drawings, graphs illustrating the use of the bioreactor in the production of the recombinant enzyme β-lactamase, are shown. β-lactamase production was monitored in bioreactors operated with growth medium containing 200 mM (FIG. 6A) or 400 mM buffer (FIG. 6B).

From FIG. 6, it can be observed that there was an initial lag in β-lactamase production in the first 14-22 hours of operation. This was due to the initial accumulation of biomass until a sufficiently thick biofilm was obtained to allow the establishment of nutrient gradients across the biofilm, as well as sufficiently high levels of lactic acid produced additionally to induce the formation of β-lactamase. Biomass accumulation was more rapid in growth medium buffered with a lower molarity buffer, this was reflected in the earlier onset of β-lactamase activity when using 200 mM buffered medium (FIG. 6A). The sharper increase in β-lactamase production observed when using 400 mM buffered medium (FIG. 6B) highlights the pH-regulated induction mechanism of the P170 expression system. Production can be seen to be extended well beyond 30 hours.

Levels of productivity recorded for bioreactors operated using 200 mM or 400 mM buffered growth medium are listed in Table 4. On average, higher maximum concentrations were observed when cultured using 400 mM buffered medium (Table 4) with a maximum of 24 685 Units/l recorded. Volumetric productivities did not differ significantly between different growth medium but was rather correlated with increased flux. Higher flux may both maintain the pH within the optimal production range (pH 5.5-6.5) and improve product solubility, particularly in growth medium with higher salt concentration.

Secretion of product into permeate limits contamination by intracellular proteins, negates the need for biomass removal through centrifugation and facilitates simpler downstream purification processes.

TABLE 3

Composition L. Lactis Growth Medium

| Component | LM5-V100-G75 |
|---|---|
| FeSO4 | 50 μM |
| CaCl2 | 2.5 μM |
| MgCl2 | 2.6 mM |
| (NH4)6Mo7O24 | 15 nM |
| H3BO3 | 2.0 μM |
| CoCl2 | 150 nM |
| CuSO4 | 50 nM |
| MnCl2 | 400 nM |
| ZnSO4 | 50 nM |
| K2SO4 | 1.38 mM |
| KH2PO4/K2HPO4 | 200 mM/400 mM |
| Biotin | 0.5 mg/l |
| Folic acid | 5 mg/l |
| Riboflavin | 5 mg/l |
| Niacinamide | 5 mg/l |
| Thiamin•HCl | 5 mg/l |
| Ca-Pantothenate | 5 mg/l |
| Pyridoxal•HCl | 10 mg/l |
| Glucose | 75 g/l |
| Na-Acetate | 14.7 mM |
| Yeast Extract | 15 g/l |
| Citric acid | 0.5 mM |
| L-Arginine | 1.0 g/l |
| L-Glutamine | 0.5 g/l |
| L-Serine | 1.5 g/l |

TABLE 4

β-lactamase activity and volumetric productivity recorded for bioreactors operated using 200 mM or 400 mM phosphate buffered growth medium (pH 7.2). Means were calculated for each bioreactor over a 33 hour period from T = 20 hrs to T = 53 hrs post-inoculation.

| | mM Buffer | β-lactamase Activity (U/l) | | | Volumetric Productivity (U/h per l. reactor vol.) | | |
|---|---|---|---|---|---|---|---|
| | | Max | Mean | SD | Max | Mean | SD |
| SFR 1 | 200 | 15629 | 10738 | 3746 | 9150 | 5121 | 1994 |
| SFR 11 | 200 | 11918 | 7306 | 2630 | 6054 | 2842 | 1613 |
| SFR 3 | 200 | 18472 | 10561 | 4305 | 9418 | 4369 | 1970 |
| SFR 4 | 200 | 10914 | 7574 | 2443 | 11604 | 5999 | 3087 |
| SFR 5 | 200 | 16434 | 9198 | 3698 | 13518 | 6694 | 3568 |
| SFR 6 | 200 | 17382 | 10814 | 4798 | 9260 | 4176 | 2126 |
| SFR 9 | 200 | 14963 | 8592 | 3649 | 11283 | 4887 | 3417 |
| SFR 10 | 400 | 24685 | 8424 | 8119 | 12006 | 3287 | 3881 |
| SFR 12 | 400 | 23308 | 11010 | 6541 | 7056 | 3819 | 2479 |
| SFR 7 | 400 | 16602 | 10005 | 3748 | 9442 | 5307 | 2184 |
| SFR 8 | 400 | 21682 | 11672 | 6335 | 18183 | 5910 | 5576 |

Example 3

*Escherichia coli* pBAD/gIII Expression System (Invitrogen)

The pBAD/gIII plasmid is a pBR3222-derived expression vector designed for regulated, secreted recombinant protein expression and purification in *E. coli*. The gene III signal sequence is used to secrete the recombinant protein into the periplasmic space. The araBAD promoter regulates expression, induced by L-arabinose. The concentration of inducer controls the level of expression. This can be optimized for soluble protein production. The araBAD promoter is repressed in the absence of L-arabinose and in the presence of glucose.

Strain & Culture Conditions:
 *E. coli* TOP 10 competent cells were transformed with the control plasmid pBAD/gIII/Calmodulin (Calmodulin producing) as described for the Invitrogen pBAD/gIII expression kit (Cat. No. V450-01). Inoculum was prepared from a single colony inoculating 20 ml Terrific Broth with 100 μg/ml ampicillin (Table 2) and incubated for 16 hours at 37° C., 200 rpm. Optimal pH for induction is between pH 4-8.

Bioreactor Setup:
 Bioreactors were manifolded into banks in which medium supply was regulated using a single source of compressed air. Each bioreactor within a given bank was supplied with nutrients from its own medium supply vessel. Growth medium used for Calmodulin production was Terrific Broth with 100 μg/ml ampicillin. Medium was also spiked with 0.0625 M NaNO$_3$ to promote anaerobic growth. Four banks of three bioreactors each were used to examine four different levels of inducer.

Different banks were spiked as follows:
BANK 1: 0.0625 M NaNO$_3$
BANK 2: 0.0625 M NaNO$_3$+0.00002% L-arabinose
BANK 3: 0.0625 M NaNO$_3$+0.002% L-arabinose
BANK 4: 0.0625 M NaNO$_3$+2% L-arabinose Inoculation & Operation:
 Bioreactors were autoclaved and set up for anaerobic operation according to SOPs. Sterile growth medium was dispensed into each of the medium supply vessels prior to starting the experiment.

Bioreactors were each inoculated with 1 ml overnight culture of *E. coli* pBAD/gIII/Calmodulin. Inoculum was injected directly into the ECS of each bioreactor according to SOP.

Following inoculation, medium was supplied to each bioreactor at 5 kPa. Pressures were increased incrementally in order to immobilize biomass, limit planktonic growth and prevent backgrowth into nutrient supply vessels. Pressures were adjusted as follows:

TABLE 5

| Time post-inoculation (hrs) | Pressure (kPa) |
|---|---|
| 0 | 5 |
| 4 | 10 |
| 5 | 15 |
| 7 | 30 |
| 8 | 80 |
| 20 | 100 |

Analysis 24 hours post-inoculation, capillary membrane inserts were removed from each bioreactor module and placed in a clean 50 ml centrifuge tube. Using replicate cultures, Calmodulin was extracted from biofilms using procedures described in the Invitrogen pBAD/gIII instruction manual:

1) Osmotic shock procedure: each biofilm was treated with 10 ml ice cold Osmotic Shock solution 1 for 10 minutes, centrifuged at 4000 rpm for 10 min and the supernatant discarded. The pellet was treated twice with 10 ml ice cold Osmotic Shock solution 2 for 10 min, centrifuged at 4000 rpm for 10 min. Supernatants were combined and stored at −20° C.
2) Cell lysis procedure: each biofilm was resuspended in 10 ml cell lysis buffer with 2 freeze/thaw cycles. Samples were microfuged at 14 000 rpm for 2 min, the supernatant removed and stored at −20° C.
3) Direct analysis: biofilms were each resuspended in 2 ml SDS-PAGE denaturing loading buffer and stored at −20° C. Calmodulin production was monitored by SDS-PAGE.

Growth & Productivity

From Table 6, biomass yield per 20 ml bioreactor was similar under all growth conditions. A maximum cell density of 7.9 g dry cell weight per liter reactor volume was obtained after 24 hours. Soluble protein extracted from biofilms using the osmotic shock procedure showed limited induction of Calmodulin production with 0.00002% L-arabinose in comparison to the uninduced control. At 0.002% L-arabinose showed a 1.2-fold increase in protein synthesis while induction with 2% L-arabinose showed a 2.8-fold increase in protein produced per mg dry cell weight.

TABLE 6

Dry cell weight of cells and total soluble protein extracted from biofilm using osmotic shock procedure, as produced per 20 ml bioreactor cultured with different levels of the inducer L-arabinose.

|  | Control | 0.00002% L-arabinose | 0.002% L-arabinose | 2% L-arabinose |
| --- | --- | --- | --- | --- |
| mg Dry Cell Weight | 141 | 134 | 158 | 136 |
| Dry cell weight per l. reactor vol. | 7.1 g | 6.7 g | 7.9 g | 6.8 g |
| µg/ml Protein | 2.1 | 2.1 | 3.0 | 5.8 |
| µg Protein | 42.9 | 42.3 | 59.0 | 116.7 |
| µg Protein/mg Dry Cell Weight | 0.304 | 0.316 | 0.374 | 0.858 |

Figure 7A:
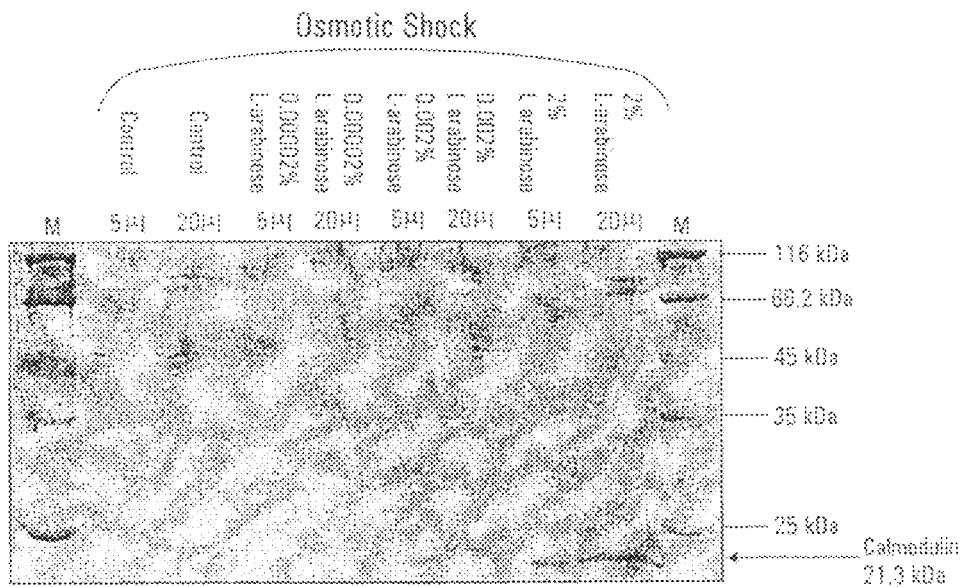
FIGS. 7A and 7B are photographs of SDS-PAGE gels showing Calmodulin production by *E. coli* pBAD/gIII/Calmodulin in bioreactors cultured with growth medium containing 0% (control), 0.00002%, 0.002% or 2% of the inducer molecule, L-arabinose. (A) Protein extracts prepared from biofilms by osmotic shock procedure. (B) Protein extracts prepared by direct analysis of biofilms in denaturing sample buffer or the soluble fraction of cell lysis procedure.
Figure 7B:
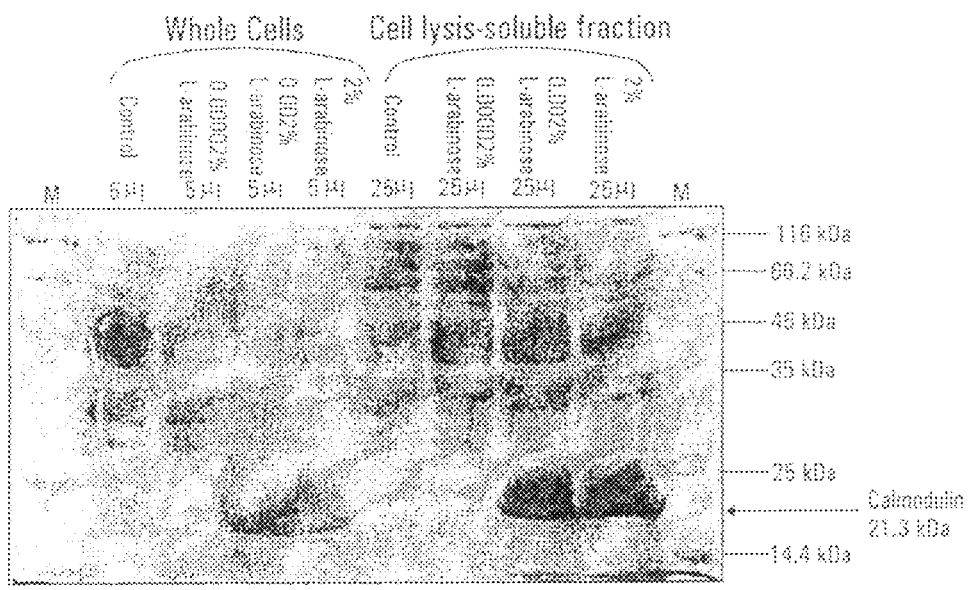

FIG. 7 shows recombinant protein production by *E. coli* pBAD/gIII/Calmodulin using bioreactors extracted using the osmotic shock procedure (FIG. 7A) or through cell lysis and direct analysis (FIG. 7B). No induction was detected in control bioreactors (no inducer) nor bioreactors treated with 0.00002% L-arabinose. Soluble calmodulin extracted using osmotic shock showed improved productivity with an increase in the level of L-arabinose (FIG. 7A). The osmotic shock extract showed a higher level of purity in comparison to protein preparations from cell lysis or whole cell extracts prepared from replicate cultures (FIG. 7B).

Nutrient gradients established across the developing biofilm allowed for the derepression of the araBAD promoter, while increased levels of the inducer molecule L-arabinose supplied in the growth medium facilitated induction of expression. Higher levels of soluble protein were extracted from cells through cell lysis, however a purer product was achieved through osmotic shock. This procedure can further be optimized and performed in situ; extracting proteins into permeate while retaining cells, negating the need for centrifugation steps and integrated with simpler downstream processing solutions.

REFERENCES

1. Davis, D. A., Lynch, H. C. and Varley, J. (1999) The production of Surfactin in batch culture by *Bacillus subtilis* ATCC 21332 is strongly influenced by the conditions of nitrogen metabolism. Enzyme and Microbial Technology 25, pp. 322-329.
2. Georgiou, G., Lin S-C. and Sharma M. M. (1992) Surface active compounds from microorganisms. Biotechnol. 10, pp. 60-64.
3. Vollenbrioch D., Ozel, M., Vater, J., Kamp, R. M. and Pauli, G. (1997a) Mechanism of inactivation of enveloped viruses by surfactin from *Bacillus subtillis*. J. Gen. Microbiol. 25, pp. 289-297.
4. Vollenbrioch, D., Pauli, G., Ozel, M. and Vater, J. (1997b) Antimycoplasma properties and application in cell culture of surfactin, a lipopeptide antibiotic from *Bacillus subtillus*. Appl. Environ. Microbiol. 63, pp. 44-49.
5. Bernheimer, A. W. and Avigad, L. S (1970) Nature and properties of a cytolytic agen produced by *Bacillus subtillis*. J. Gen. Microbiol. 61, pp. 361-369.
6. Nakano, M. N. and Hulett, F. M. (1999) Adaptation of *Bacillus subtillis* to oxygen limitation. FEMS Microbiol. Lett. 157, pp. 1-7.
7. Cooper D. G., MacDonald, C. R., Duff, S. F. B. and Kosaric, N. (1981) Enhanced production of surfactin from *Bacillus subtillis* by continuous product removal and metal cation additions. Appl. Environ. Microbiol. 42, pp. 408-412.
8. Wei, Y. H. and Chu I. M. (1998) Enhancement of surfactin production in iron-enriched media by *Bacillus subtillis* ATCC 21332. Enzyme Microbial Technol. 22, pp. 724-728.
9. Wei, Y. H., Wang L. F., Chang J. S. and Kung S. S. (2003) Identification of induced acidification in iron-enriched cultures of *Bacillus subtillis* during biosurfactant fermentation. J. Bioscience and Bioeng. 96, pp. 174-178.
10. Wei Y. H., Wang L. F. and Chang J. S. (2004) Optimizing iron supplement strategies for enhanced surfactin production with *Bacillis subtillis*. Biotechnol Prog. 20, pp. 979-983.
11. Davis, D. A., Lynch, H. C. and Varley, J. (2001) The application of foaming for the recovery of surfactin from *B. subtillis* ATCC 21332 cultures. Enzyme Microbial Technol. 28, pp. 346-354.
12. Yeh, M. S., Wei, Y. H. and Chang J. S. (2006) Bioreactor design for enhanced carrier-assisted surfactin production with *Bacillus subtillis*. Process Biochem. 41, 1799-1805.
13. Studier, W. F. (2005). Protein production by auto-induction in high-density shaking cultures. Protein Expression and Purification 41, pp. 207-234
14. de Vos (1999). Gene Expression systems for lactic acid bacteria. Current Opinion in Microbiology 2, pp. 289-295.
15. Kuipers, O. P., Pascalle, G. G. A.; Kleerebezem, M and de Vos, W. M. (1997). Controlled overproduction of proteins by lactic acid bacteria. TiBTech 15, pp. 135-140.
16. Xu Xia Zhou, Wei Fen Li, Guo Xia Ma and Yuan Jiang Pan. (2006) The nisin-controlled gene expression system: Construction, application and improvements. Biotech. Advances 24, pp. 285-295.
17. Madsen, S. M., Arnau, J., Vrang, A., Givskov M. and Israelsen H. (1999) Molecular characterization of the pH-inducible and growth phase-dependent promoter P170 of *Lactococcus lactis*. Mol. Microbiol. 32, pp. 75-87

A number of embodiments of the invention have been described. Nevertheless, it will be understood that various modifications can be made without departing from the spirit and scope of the invention.

The invention claimed is:
1. A method of producing secondary metabolites under oxygen-limited or anaerobic culture conditions in a bioreactor, the method comprising:
    providing a bioreactor comprising:
        a reactor housing defining an extracapillary space;
        a porous tubular hollow fiber substrate having a first external surface side and a second inner lumen side, the porous tubular hollow fiber substrate being configured to allow the passage of secondary metabolites therethrough and to prevent the passage of microorganism cells therethrough; and a feeding arrangement supplying a nutrient solution to the extracapillary space under pressurized conditions;

inoculating the bioreactor extracapillary space with microorganisms to establish a biofilm of microorganisms attached to the first external surface side of the substrate, the biofilm of microorganisms having a membrane/substrate interface between the substrate and the biofilm of microorganisms; and causing a nutrient solution to flow under pressure through the biofilm and the substrate in direction from the first external surface side thereof to the second inner lumen side thereof under anaerobic culture conditions, at a rate which is sufficiently low for a nutrient gradient to be established across the biofilm such that the nutrient concentration is high at an outer surface of the biofilm and sufficiently high to support exponential growth of the microorganisms, and wherein the nutrient concentration is low closer to the substrate and sufficiently low to induce and sustain a stationary phase of the microorganisms and thereby cause the microorganisms to produce at least one secondary metabolite, the flow of the nutrient solution through the substrate carrying said secondary metabolite through the substrate to the second inner lumen side thereof where secreted secondary metabolite can be collected, with the microorganism cells from the biofilm being retained at the external surface first side thereof, wherein the pressure at which the nutrient solution is caused to flow through the biofilm and the substrate is increased over time from 5 to 100 kPa to sustain and maintain the stationary phase of the microorganisms at the membrane/substrate interface between the substrate and the biofilm of microorganisms.

2. The method of claim 1, wherein the microorganisms are selected from the group consisting of *Clostridium* sp., *Bacillus* sp., *Pseudomonas* sp., *Vibrio* sp., *Rhodopseudomonas* sp., *Desulphovibrio desulfuricans*, and *Candida* sp.

3. The method of claim 1, wherein the nutrient solution flow rate from the first side to the second side is a function of a volume of the bioreactor such that the nutrient solution flow rate per hour from the first side to the second side is about 0.01 times the volume of the bioreactor to about 10 times the volume of the bioreactor.

4. The method of claim 1, further comprising carrying out the method at a temperature between 2-109° C.

5. The method of claim 1, further comprising carrying out the method at an initial pH between 1-13.

6. The method of claim 1, further comprising carrying out the method for a period between 1-30 days.

7. The method of claim 1, wherein the biofilm of microorganisms has a thickness of 0.1-10 mm.

8. The method of claim 1, further comprising producing the secondary metabolite intracellularly by the microorganisms.

9. The method of claim 1, further comprising producing the secondary metabolite intracellularly by the microorganisms, whereafter the secondary metabolite is secreted from the microorganism into the extracellular environment.

10. A method of producing at least one recombinant product under oxygen-limited or anaerobic culture conditions in a bioreactor, the method comprising:

providing a bioreactor comprising:
a reactor housing defining an extracapillary space;
a porous tubular hollow fiber substrate having a first external surface side and a second inner lumen side, the porous tubular hollow fiber substrate being configured to allow the passage of recombinant product therethrough and to prevent the passage of microorganism cells therethrough; and a feeding arrangement supplying a nutrient solution to the extracapillary space under pressurized conditions;

inoculating the bioreactor extracapillary space with microorganisms to establish a biofilm of microorganisms attached to the first external surface side of the substrate, the biofilm of microorganisms having a membrane/substrate interface between the substrate and the biofilm of microorganisms; and causing a nutrient solution to flow under pressure through the biofilm and the substrate in direction from the first external surface side thereof to the second inner lumen side thereof under anaerobic culture conditions, at a rate which is sufficiently low for a nutrient gradient, having a concentration differential, to be established across the biofilm such that the nutrient concentration is high at an outer surface of the biofilm and sufficiently high to support exponential growth of the microorganisms, and wherein the nutrient concentration is low closer to the substrate and sufficiently low to induce and sustain a stationary phase of the microorganisms and thereby to induce production of at least one recombinant product by the microorganisms, the flow of the nutrient solution through the substrate carrying the recombinant product through the substrate to the second inner lumen side thereof where the recombinant product can be collected, with the microorganism cells from the biofilm being retained at the external surface first side thereof, wherein the pressure at which the nutrient solution is caused to flow through the biofilm and the substrate is increased over time from 5 to 100 kPa to sustain and maintain the stationary phase of the microorganisms at the membrane/substrate interface between the substrate and the biofilm of microorganisms.

11. The method of claim 10, wherein the microorganisms are selected from the group consisting of *Lactococcus lactis, Escherichia coli, Bacillus subtillus, Pichia* sp., *Candida* sp., *Hansenula polymorpha* and *Sacharomyces cerevisiae*.

12. The method of claim 10, further comprising carrying out the method at a temperature between 2-109° C.

13. The method of claim 10, further comprising the carrying out the method at an initial pH between 1-13.

14. The method of claim 10, further comprising carrying out the method for a period between 1-30 days.

15. The method of claim 10, wherein the nutrient solution flow rate from the first side to the second side is a function of a volume of the bioreactor such that the nutrient solution flow rate per hour from the first side to the second side is about 0.01 times the volume of the bioreactor to about 10 times the volume of the bioreactor.

16. The method of claim 10, wherein the biofilm of microorganisms has a thickness of 0.1-10 mm.

17. The method of claim 10, further comprising adding an inducer molecule to the nutrient solution such that the flow of the nutrient solution through the substrate carries said inducer molecule through the biofilm from the first side to the second side, thereby to induce production of said recombinant product by the microorganisms.

18. The method of claim 17, wherein the inducer is selected from at least one of L-arabinose, isopropyl b-D-thiogalactoside (IPTG) and methanol.

19. The method of claim 17, wherein the inducer molecule includes a secondary metabolite that is produced intracellularly by the microorganisms.

20. The method of claim 17, wherein the inducer molecule includes a secondary metabolite that is produced intracellularly by the microorganisms, whereafter the secondary metabolite is secreted from the microorganism into the extracellular environment.

* * * * *